US012661161B2

(12) United States Patent (10) Patent No.: US 12,661,161 B2
Hammann et al. (45) Date of Patent: Jun. 23, 2026

(54) SPINAL COMPRESSION INSTRUMENT AND RELATED METHODS

(71) Applicant: NuVasive, Inc., San Diego, CA (US)

(72) Inventors: Conrad Tyler Hammann, Carlsbad, CA (US); Scott Lish, Oceanside, CA (US)

(73) Assignee: Globus Medical Inc., Audubon, PA (US)

( * ) Notice: Subject to any disclaimer, the term of this patent is extended or adjusted under 35 U.S.C. 154(b) by 8 days.

(21) Appl. No.: 18/787,336

(22) Filed: Jul. 29, 2024

(65) Prior Publication Data

US 2024/0382239 A1 Nov. 21, 2024

Related U.S. Application Data

(63) Continuation of application No. 17/231,831, filed on Apr. 15, 2021, now Pat. No. 12,070,252, which is a continuation of application No. 16/268,237, filed on Feb. 5, 2019, now Pat. No. 11,006,983, which is a continuation of application No. 15/367,783, filed on Dec. 2, 2016, now Pat. No. 10,194,960.

(60) Provisional application No. 62/262,491, filed on Dec. 3, 2015.

(51) Int. Cl.
| *A61B 17/88* | (2006.01) |
| *A61B 17/70* | (2006.01) |
| *A61B 17/00* | (2006.01) |
| *A61B 17/56* | (2006.01) |
| *A61B 17/68* | (2006.01) |

(52) U.S. Cl.
CPC ...... *A61B 17/7086* (2013.01); *A61B 17/7079* (2013.01); *A61B 17/708* (2013.01); *A61B* *2017/00407* (2013.01); *A61B 2017/564* (2013.01); *A61B 2017/681* (2013.01)

(58) Field of Classification Search
CPC ............ A61B 17/7086; A61B 17/7079; A61B 17/708; A61B 2017/00407; A61B 2017/564; A61B 2017/681
USPC .................. 606/86 A, 105, 279, 246, 265, 99
See application file for complete search history.

(56) References Cited

U.S. PATENT DOCUMENTS

| | | | | |
|---|---|---|---|---|
| 5,167,662 A * | 12/1992 | Hayes | ................ | A61B 17/7047 606/151 |
| 12,070,252 B2 * | 8/2024 | Hammann | ......... | A61B 17/7079 |
| 2006/0009777 A1 * | 1/2006 | Lim | .................... | A61B 17/8019 606/90 |
| 2011/0184469 A1 * | 7/2011 | Ballard | .............. | A61B 17/7086 606/279 |
| 2014/0058464 A1 * | 2/2014 | Hutchens | ........... | A61B 17/7086 606/86 A |

* cited by examiner

*Primary Examiner* — Eduardo C Robert
*Assistant Examiner* — David C Comstock

(57) ABSTRACT

The disclosure provides systems and instruments that allow vigorous compression of two bone structures while minimally impeding visual access to the surgical site. This is achieved by use of a sleeve member that connects a stanchion to a lever. The system includes a stanchion member, a sleeve member dimensioned to at least partially encircle the stanchion member, and a compression lever including. The sleeve and the lever form a pivot point to allow the compression lever to rotate relative to the stanchion member when the sleeve is reversibly placed around the stanchion member.

13 Claims, 8 Drawing Sheets

SPINAL COMPRESSION INSTRUMENT AND RELATED METHODS

CROSS-REFERENCE TO RELATED APPLICATIONS

This application is a continuation of U.S. Ser. No. 17/231,831 (published as US 2021-0228246), filed Apr. 15, 2021, which is a continuation of U.S. Ser. No. 16/268,237 (now U.S. Pat. No. 11,006,983), filed Feb. 5, 2019, which is a continuation of U.S. Ser. No. 15/367,783 (now U.S. Pat. No. 10,194,960), filed Dec. 2, 2016, which claims the benefit of U.S. Ser. No. 62/262,491, filed Dec. 3, 2015, all of which are incorporated herein by reference in their entireties.

FIELD

The present disclosure relates generally to medical devices, and specifically to surgical instruments and methods for performing spinal fixation.

BACKGROUND

The spine is critical in human physiology for mobility, support, and balance. The spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination.

Surgical procedures on the spine often include the immobilization of two or more vertebra. Immobilizing the vertebrae may be accomplished in many ways (e.g. fixation plates and pedicle screw systems). One of the most common methods for achieving the desired immobilization is through the application of bone anchors (most often introduced into the pedicles associated with the respective vertebra to be fixed) that are then connected by rigid rods locked to each pedicle screw. Once immobilized, the patient's bone will ideally grow between the immobilized vertebrae, creating a permanent stable boney structure. In addition to the bone anchor construct, interbody implants are often deposited in the disc space to restore and maintain the height of the disc space while fusion occurs and to provide a scaffold for bone growth.

Compression across an interbody implant promotes bone growth and fusion. Such compression is often achieved using specialized tools, as is known in the art. When performing less invasive spinal surgical procedures (e.g., one or two level transforaminal lumbar interbody fusion {TLIF) and posterior lumbar interbody fusion (PUF), it can be difficult for the surgeon to achieve robust compression due to limited exposure of the vertebral surfaces and the use of small incisions. Some compressors sacrifice strength in order to increase visualization, resulting in flimsy arms which can flex and deliver inferior compressive load. Others increase strength but diminish visualization, making instrument attachment a challenge. Still others have a tubular counter-torque as a fulcrum point to provide a robust compression platform, but also require the user to hold the compression until a lock screw Is delivered (often requiring a second person} to hold the compression.

There is a need in the art for an instrument that can deliver high compression loads without sacrificing the visibility of the surgical site, and which further can be used without the need for second or additional persons working in the incision.

SUMMARY

The present disclosure describes systems, instruments, and methods for vertebral compression amenable to less invasive surgical procedures. For example, a pedicle screw compression system for use in a minimally invasive, and/or TLIF/PUF surgical procedure is described. This is generally a single level surgical technique which may use a retractor for access, The pedicle screw compression system includes a compressor working in conjunction with a tubular counter torque to apply a compressive force between two screw tulips. The compressor comprises an elongated lever member that pivots about a sleeve member, which attaches to the tubular counter torque. By squeezing the compressor lever towards the tubular counter torque at the proximal end, a compressive force Is delivered between two tulips at the distal end, The pedicle screw compression system also employs a ratchet mechanism to maintain the compression, thus freeing the users' second hand to deliver a lock screw through the tubular counter torque.

The sleeve member fits around the tubular counter torque, and includes a flexible retention feature to dip onto the tube and maintain assembly, The sleeve also transfers the compressive load from the compressor lever to the counter torque shaft. The compressor lever interacts with the second tulip to apply the compressive load. This is coupled to the sleeve member through the pivot point. The ratchet mechanism comprises a spring loaded toothed plunger that is housed within the compressor lever body. This plunger is biased forward, and has a distal end including ratchet teeth that locks into a corresponding toothed surface on the sleeve member as compression is delivered. The ratchet release button pulls the ratchet plunger upward and releases the compressive load when desired. The separate sleeve member component allows for the pivot point to shift to the opposite side of the tubular counter torque, which increases the compressor lever throw and allows for the addition of a toothed ratchet surface on the back face of the sleeve member. The sleeve also creates a more robust assembly with the counter torque than a single piece instrument would.

Now according to a first aspect, a spinal compression system for compressing a first bone structure relative to a second bone structure is provided, the system comprising: a stanchion member having an elongate shaft and a first bone anchor engagement feature; a sleeve member dimensioned to at least partially encircle the stanchion member, the sleeve member comprising a first part of a pivot mechanism; and a compression lever including; a second bone anchor engagement feature at a distal end, and a second part of the pivot mechanism that reversibly connects to the first part of the pivot mechanism forming a pivot point to allow the compression lever to rotate relative to the stanchion member about an axis that contains the pivot point.

In a second aspect, a spinal compression instrument for compressing a first bone structure relative to a second bone structure is provided, the instrument comprising: a stanchion member having an elongate shaft and a first bone anchor engagement feature; a sleeve member at least partially encircling the stanchion member; and a compression lever pivotably connected to the sleeve member at a pivot point to allow the compression lever to rotate relative to the stanchion member about an axis that contains the pivot point, and including a second bone anchor engagement feature at a distal end.

In a third aspect, a method of compressing a first bone structure containing a first bone anchor relative to a second bone structure containing a second bone anchor ls provided, the method comprising: assembling a stanchion member having an elongate shaft and a first bone anchor engagement feature with a sleeve member such that the sleeve member at least partially encircles the stanchion member; pivotably connecting a compression lever including a second bone anchor engagement feature at a distal end to the sleeve member at a pivot point to allow the compression lever to rotate relative to the stanchion member about an axis that contains the pivot point; engaging the first bone anchor engagement feature to the first bone anchor; engaging the second bone anchor engagement feature to the second bone anchor; and compressing the first bone structure relative to the second bone structure by imparting force on a proximal end of the compression lever with a vector toward the stanchion member.

The above presents a simplified summary in order to provide a basic understanding of some aspects of the claimed subject matter. This summary Is not an extensive overview. It is not intended to identify key or critical elements or to delineate the scope of the claimed subject matter. Its sole purpose is to present some concepts in a simplified form as a prelude to the more detailed description that Is presented later.

DETAILED DESCRIPTION

Figure 1:
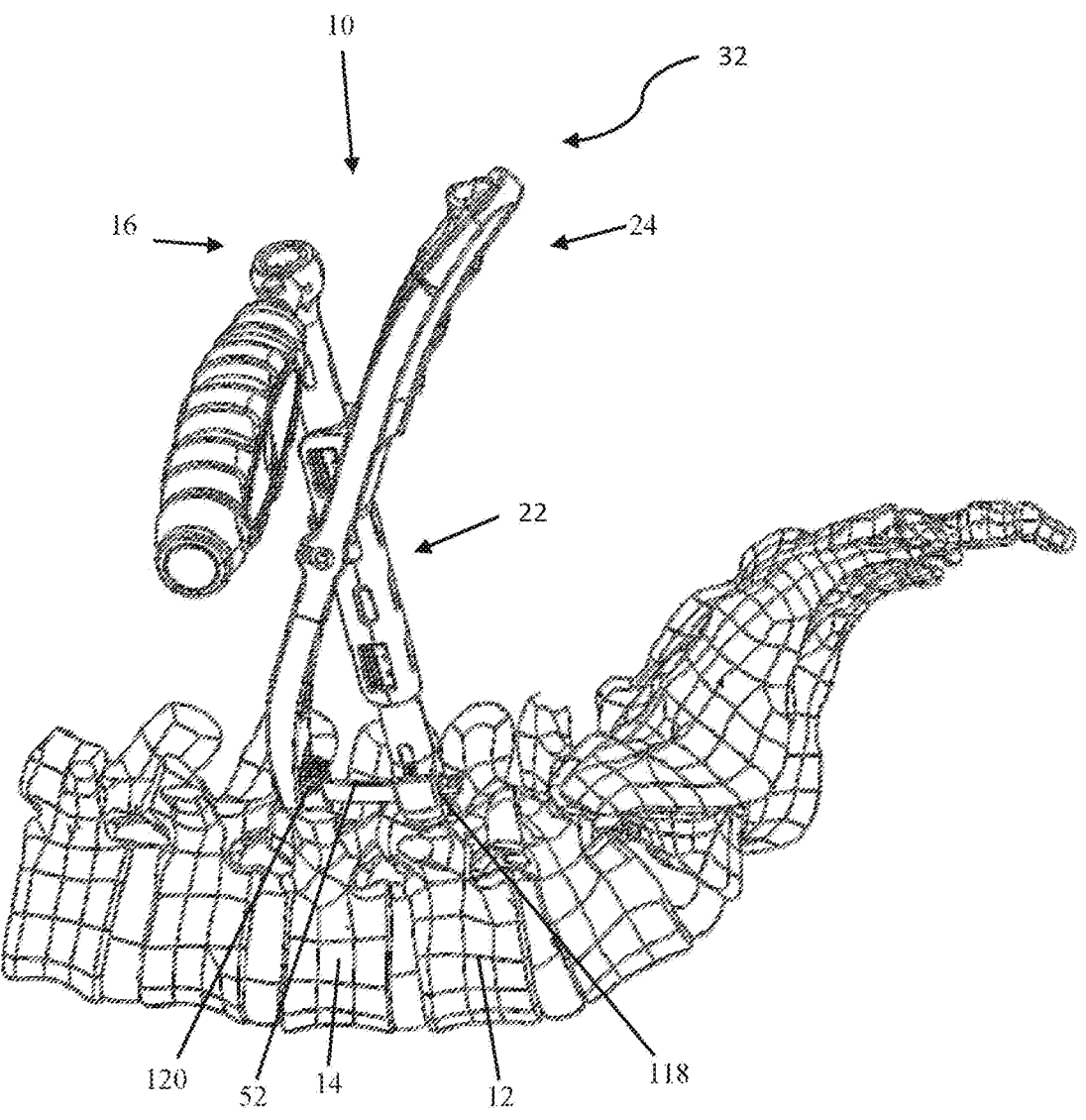
FIG. 1 is a perspective view of an example of a pedicle screw compression system in use with a spinal construct implanted on a portion of a spine, according to one embodiment.

Illustrative embodiments of a compression system 32 and instrument 10 are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill ln the art having the benefit of this disclosure. The compression system 32. and instrument 10 disclosed herein boast a variety of inventive features and components that warrant patent protection, both individually and in combination.

The disclosure provides systems 32 and instruments 10 that allow vigorous compression of two bone structures while minimally impeding visual access to the surgical site. This is achieved by use of a sleeve member 22 that connects a stanchion 16 to a lever 24. The sleeve 22 creates a very strong connection between the stanchion 16 and the lever 24 that does not appreciably increase the profile of the stanchion 1.6, and in some embodiments allows the lever 24 and the stanchion 16 to be easily assembled together and disassembled.

A general embodiment of the spinal compression system 32 comprises: a stanchion member 16 having an elongate shaft 18 and a first bone anchor engagement feature 20; a sleeve member 22 dimensioned to at least partially encircle the stanchion member 16, the sleeve member 2.2. comprising a first part 34 of a pivot mechanism 30; and a compression lever 24 including: a second bone anchor engagement feature 2.8 at a distal end 40, and a second part 36 of the pivot mechanism 30 that reversibly connects to the first part 34 of the pivot mechanism 30 forming a pivot point 26 to allow the compression lever 24 to rotate relative to the stanchion member 16 about an axis that contains the pivot point 26, The system 32 is intended to be assembled as a compression instrument 10, A general embodiment of the compression instrument 10 comprises: a stanchion member 16 having an clongate shaft 18 and a first bone anchor engagement feature 20; a sleeve member 22 at least partially encircling the stanchion member 16; and a compression lever 24 pivotably connected to the sleeve member 22 at a pivot point 26 to allow the compression lever 24 to rotate relative to the stanchion member 16 about an axis that contains the pivot point 26, and including a second bone anchor engagement feature 28 at a distal end 40.

The stanchion member 16 functions to anchor the assembled instrument 10 to one of the bone structures (12, 14}. It thus serves as a counter-torque 96 to the compression lever 24. Some embodiments of the stanchion member 16 comprise a grabbing surface 110 to allow the user to apply force directly to the stanchion member 16, although the system 32 can also function if compressing force is applied only to the compression lever 24. in such embodiments handle 112 may be present on the stanchion 16. The handle 112 may be in any configuration which facilitates the exertion of manual force on the handle 112 toward the compression lever 24, In the embodiment illustrated in FIGS. 9-10 the handle 112 is perpendicular to the longitudinal axis of the stanchion member 16. As shown in FIG. 1, the handle 112 may also be perpendicular to the plane containing the longitudinal axis of the stanchion member 16 and the longitudinal axis of the compression lever 24. Such an arrangement is ergonomically configured to allow the compression lever 24 to be compressed with the heel of the user's hand while the handle 112 of the stanchion member 16 is gripped in the closed fist of the other hand.

The elongate shaft 18 of the stanchion member 16 will be dimensioned to allow it to be at least partially encircled by the sleeve element 22 {both in terms of width and height) and will be of sufficiently sturdy construction to withstand the compressive forces necessary to reduce the distance between the two bone structures {12, 14}. The bone anchor engagement feature 46 is designed to securely and reversibly connect the stanchion member 16 to a bone anchor 120, so as to prevent deflection or detachment between the two during compression. For example, In embodiments of the stanchion 16 designed to connect to a pedicle screw 124 (as ln FIGS. 9-10), the bone anchor engagement feature 46 is a screw receptacle 126. The screw receptacle 126 is configured to securely engage at least a portion of a tulip portion 128 of a pedicle screw 124. in the illustrated embodiment the receptacle 126 further includes a rod recess 68 formed therein to allow for unencumbered passage of the spinal rod 52 through the recess 68.

The elongate shaft 18 of the stanchion member 16 may contain a lumen 70 running from the distal 84 to the proximal end 86, in which case the elongate shaft 18 is tubular. The lumen 70 is useful to allow a locking feature 78 (such as a locking screw 72) to be introduced into the bone anchor 120 through the lumen 70, and subsequently driven into place by means of a tool introduced through the lumen 70. This configuration can be advantageous, as the incision does not then need to be widened to introduce and driver the locking feature 78.

Figures 9, 10, 11, 12:
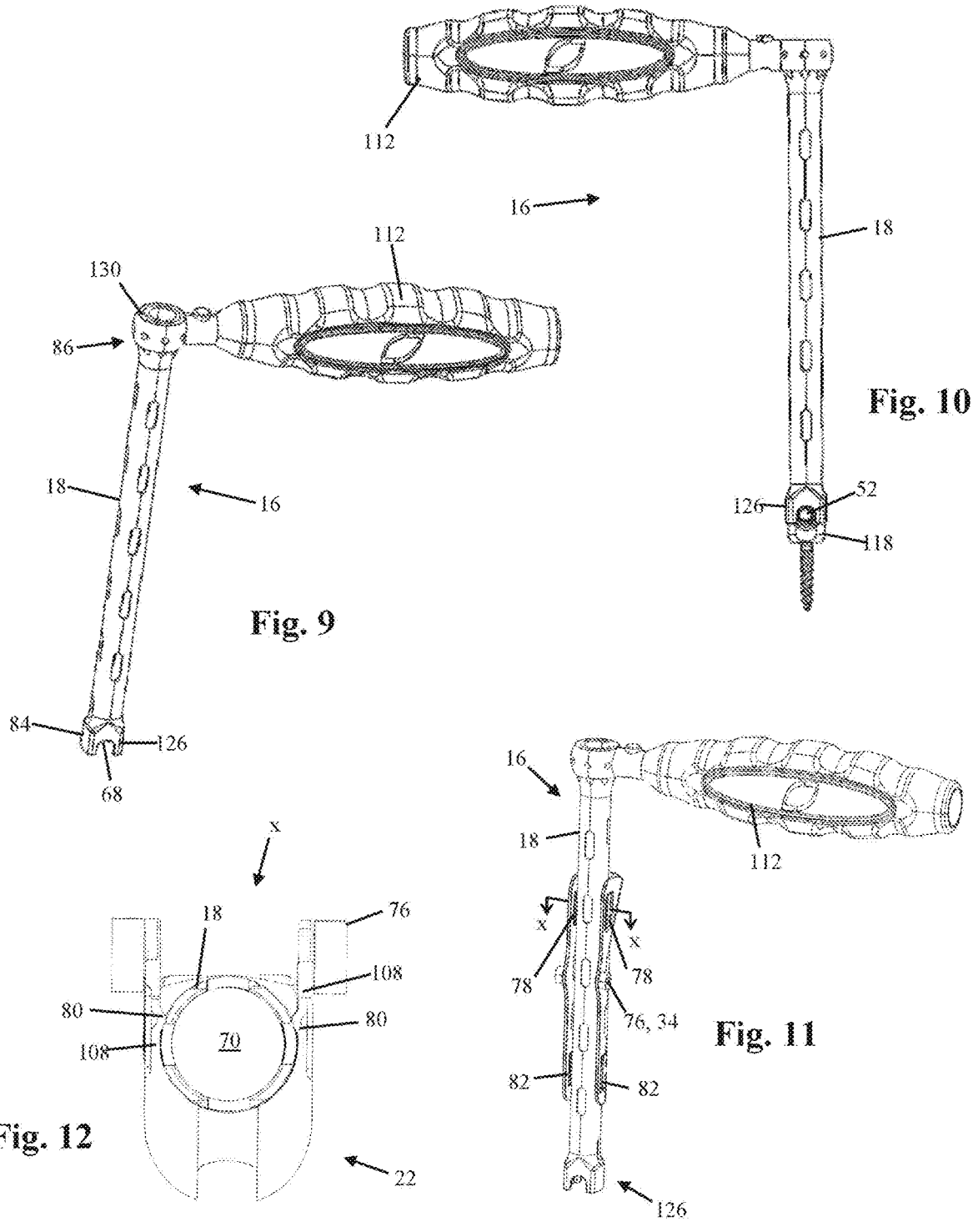
FIG. 9 Is a perspective view of an example of a stanchion member forming part of the pedicle screw compression system of FIG. L
FIG. 10 is a plan view of the stanchion member of FIG. 9, engaged with a pedicle screw.
FIG. 11 is a perspective view of the stanchion member of FIG. 9 engaged with a sleeve member of the pedicle screw compression system of FIG. 1 in isolation.
FIG. 12 is a cross-sectional view of the engaged stanchion member and sleeve of FIG. 11.
Figures 13, 14:
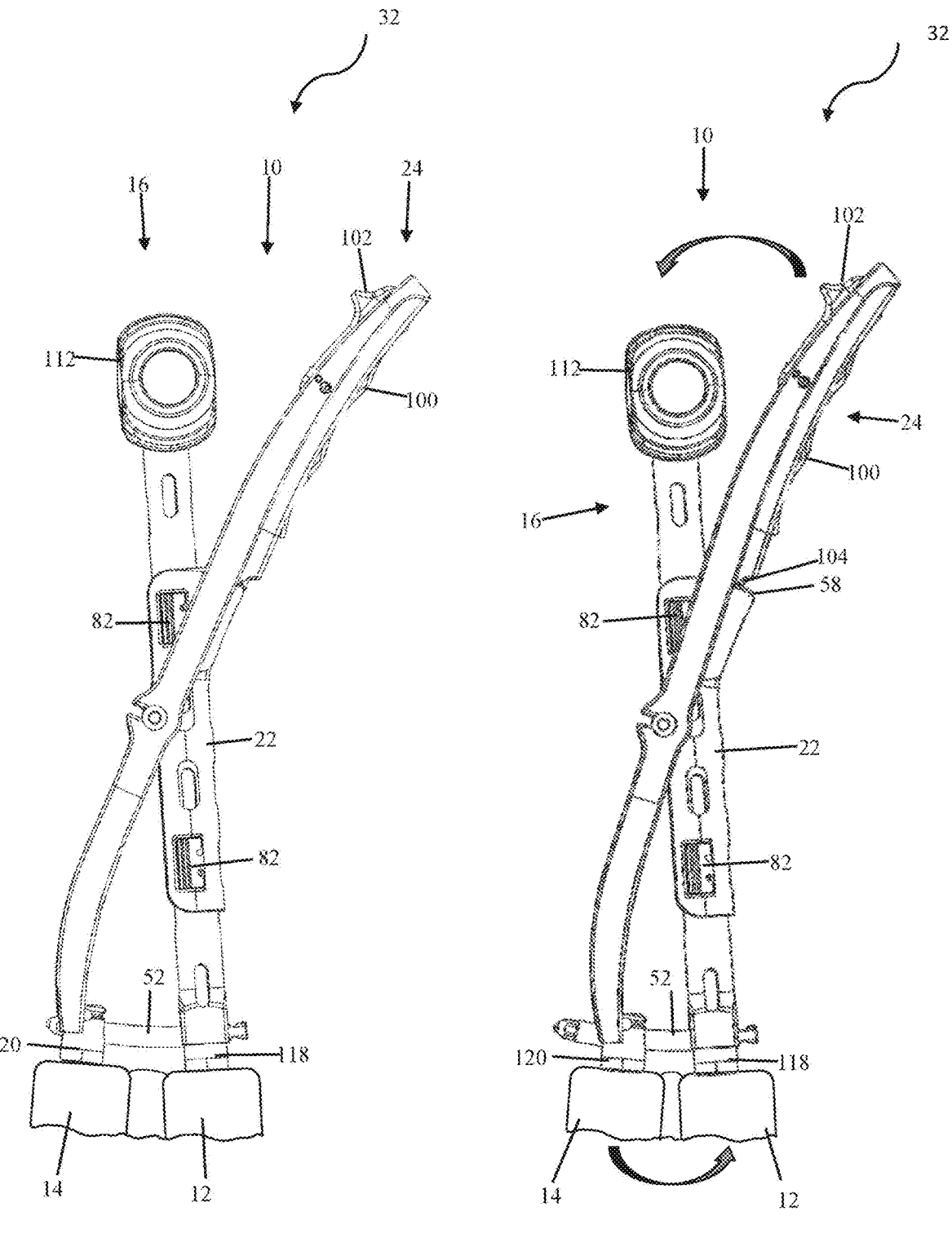
FIG. 13 is a side plan view of the pedicle screw compression system of FIG. 1 in use, prior to compression.
FIG. 14 is a side plan view of the pedicle screw compression system shown in FIG. 13, subsequent to compression {note the reduced distance between V1 and V2 compared to FIG. 13).

FIGS. 9-10 illustrate one example of the stanchion member 16 that can be described as a tubular counter torque 96. By way of example, the tubular counter torque 96 includes an elongated tubular shaft 18 (with a lumen 70 dimensioned to pass a lock screw and driver extending therethrough) coupled with a handle 112. The shaft 18 includes a distal end 84 including a screw receptacle 126 in communication with the lumen 70. The screw receptacle 126 is configured to securely engage at least a portion of a tulip portion 1.28 of a pedicle screw 124. The receptacle 126 further includes a rod recesses 68 formed therein to allow for unencumbered passage of the spinal rod 52 therethrough. The proximal end 86 of the shaft 18 includes a rotator element 130 that facilitates rotational adjustment of the handle 112 around the shaft 18 for ergonomic adjustment. FIGS. 11, 13, and 14 illustrate an embodiment of the tubular counter torque 96 as it is coupled together with the sleeve member 22 according to the snap-fit connection 82 described above.

The sleeve member 22 connects to the stanchion member 16 by at least partially surrounding it. Such partial surrounding generally refers to contact around at least 180" of the circumference of a portion of the stanchion 16. In the embodiments illustrated In FIGS. 1-7 and 11-14, the sleeve member 22 surrounds the central portion of the stanchion member 16 around about 180" of the stanchion's 16 circumference. Such a configuration has the advantage of allowing the stanchion 16 to be simply inserted and removed from the sleeve member 22, while still providing parts of the sleeve member 22 on diametrically opposed sides of the stanchion 16. One form of strong but reversible connection is a snap-fit connection 82. An example of such a snap-fit connection 82 between the sleeve member 22 and stanchion member 16 is shown in FIGS. 11-12, in which the snap-fit 82 is achieved using a plurality of flexible tabs 1.06 within the stanchion channel 90 in the sleeve 22, each flexible tab 1.08 having a ridge 80.

Some embodiments of the sleeve member 22 are configured to allow the sleeve member 22 to translate longitudinally relative to the stanchion member 16 when the two are connected. This has the advantage of allowing the pivot point 26 between the stanchion member 16 and the compression lever 24 to move during compression. One such embodiment Is the one shown in FIGS. 11-12, involving a snap-fit 82 between the stanchion member 16 and the sleeve member 22 by means of a plurality of flexible tabs 106.

Some embodiments of the sleeve member 22 are configured such that the sleeve member 22 fits around the stanchion member 16 in more than one orientation. For example, the sleeve member 22 shown in FIGS. 11-12 can be rotated 180" around its longitudinal axis and connected to the stanchion member 16. This can be useful in some embodiments if the pivot mechanism 30 is positioned off-center, resulting in a different position of the fulcrum 26 between the sleeve 22 and the compression lever 24, as discussed in more detail below.

The sleeve 22 and the compression lever 24 may be connected via a pivot mechanism 30, The pivot mechanism 30 allows the sleeve 22 and compression lever 24 to rotate relative to one another on at least one axis. In some embodiments the pivot mechanism 30 allows the sleeve member 22 and compression lever 24 to rotate relative to one another on exactly one axis. For example, the pivot mechanism 30 may comprise a pivot receptacle 74 and a pivot post 76, in the specific embodiment shown in the accompanying figures, the pivot mechanism 30 comprises a pair of pivot receptacles 74 on the sleeve 22 and a pair of pivot posts 76 on the compression lever 24. This could of course be reversed, with the posts 76 placed on the compression lever 24 and the pivot receptacles 74 on the sleeve member 22. The posts 76 and receptacles 74 may be positioned such that the pivot axis does not intersect the longitudinal axis of the sleeve member 22; such positioning creates asymmetrical location of the pivot axis depending on the orientation of the sleeve 22 over the stanchion member 16. Such embodiments have the advantage of permitting a wider variety of configurations of the assembled instrument 10.

The pivot point 26 is located along the compression lever 24 to create a class 1 or class 3 lever. In some embodiments of the compression instrument 10 the pivot point 26 is located along the compression lever 24 to create a class 1 lever. In specific embodiments of the instrument 10 the pivot point 26 is positioned to create a class 1 lever in which the distance from the pivot point 26 to the proximal end 38 of the compression lever 24 is greater than the distance from the pivot point 26 to the distal end 40 of the compression lever 24 (i.e., translates high-velocity low-force motion into low-velocity high-force motion). This increases the mechanical advantage of the lever 24, providing more precision and greater force in the compression imparted on the bone structures. In an alternate embodiment the distance from the pivot point 26 to the proximal end 38 of the compression lever 24 is about equal to the distance from the pivot point 26 to the distal end 40 of the compression lever 24.

The compression lever 24 Is manipulated to impart compressive force on the bone anchor 118 to which it is coupled (and thence to the bone structure), Such compressive force is opposed by the stanchion member 16, resulting in compressive translation of the first bone structure 12 and the second bone structure 14 toward one another (and possibly accompanying deflection). A handle grip 100 may be provided to receive manual compressive force for this purpose. For example, given that the compression lever 24 may have a proximal portion 38 and a distal portion 36, as well as a "back surface" 42 defined as the surface that faces away from the stanchion member 16, a handle grip 100 may be positioned on the back face 42 of the proximal portion 38 of the compression lever 24. A handle grip 100 in such a position may be either pushed by the heel of the user's hand or pulled with the user's fingers to provide the manual compressive force. Such a configuration is shown in FIGS. 1 and 1.3-14.

Figure 2:
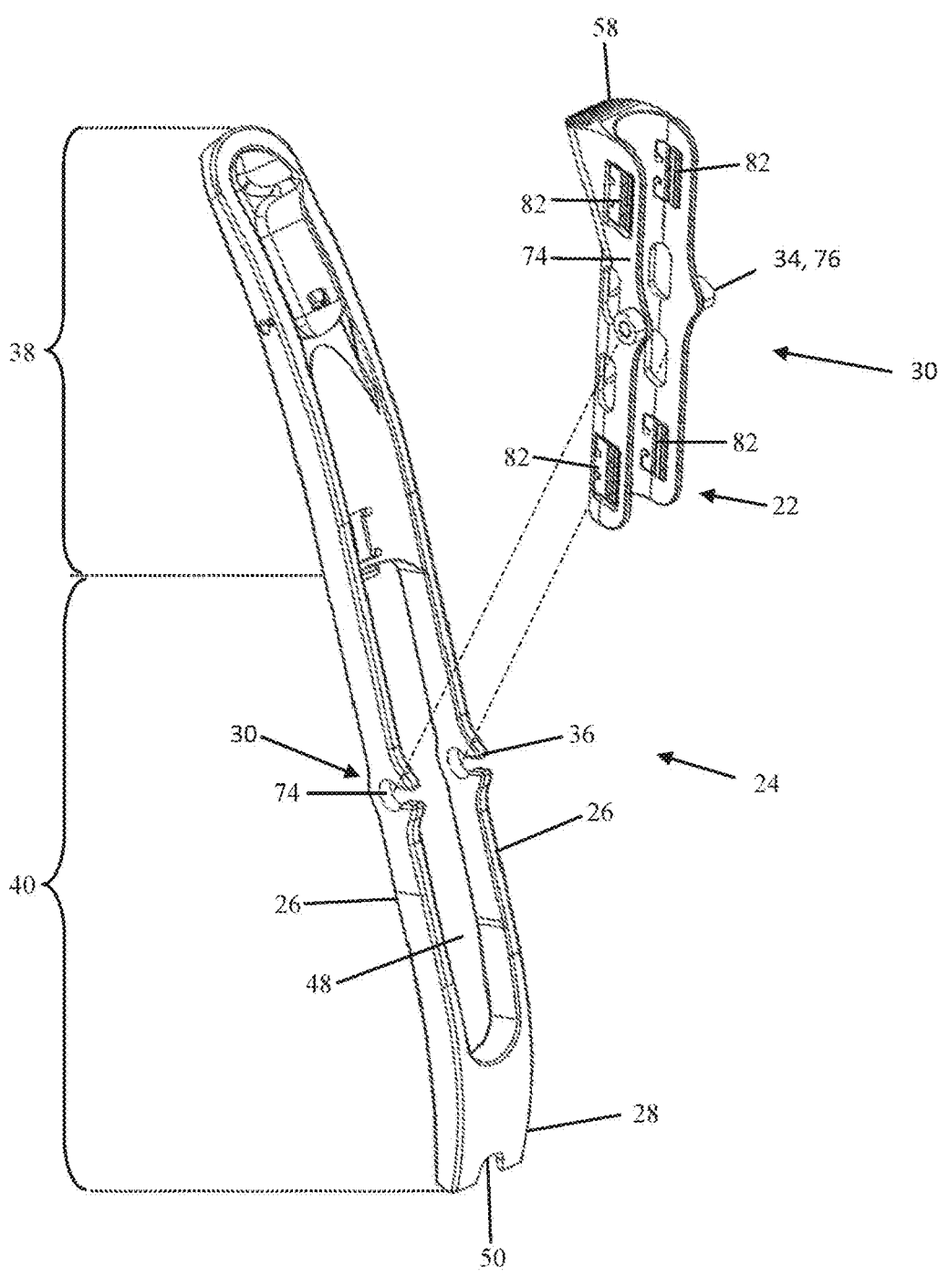
FIG. 2 is a partially exploded perspective view of an example of the compression lever and sleeve assembly forming part of the pedicle screw compression system of FIG. 1.
Figures 3, 4:
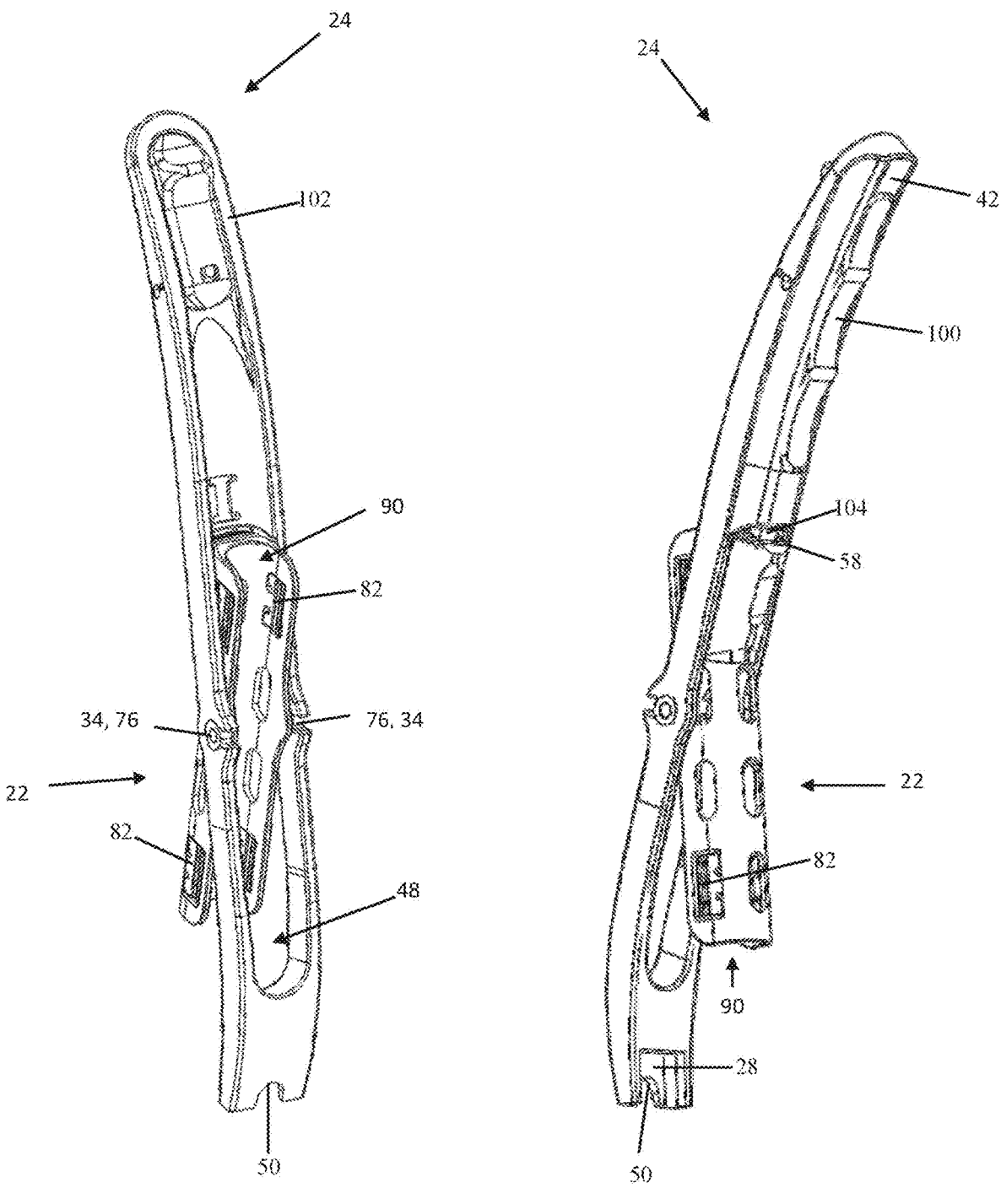
FIG. 3 is a perspective view of the compression lever and sleeve assembly of FIG. 2.
FIG. 4 is another perspective view of the compression lever and sleeve assembly of FIGS. 2-3.
Figures 5, 6:
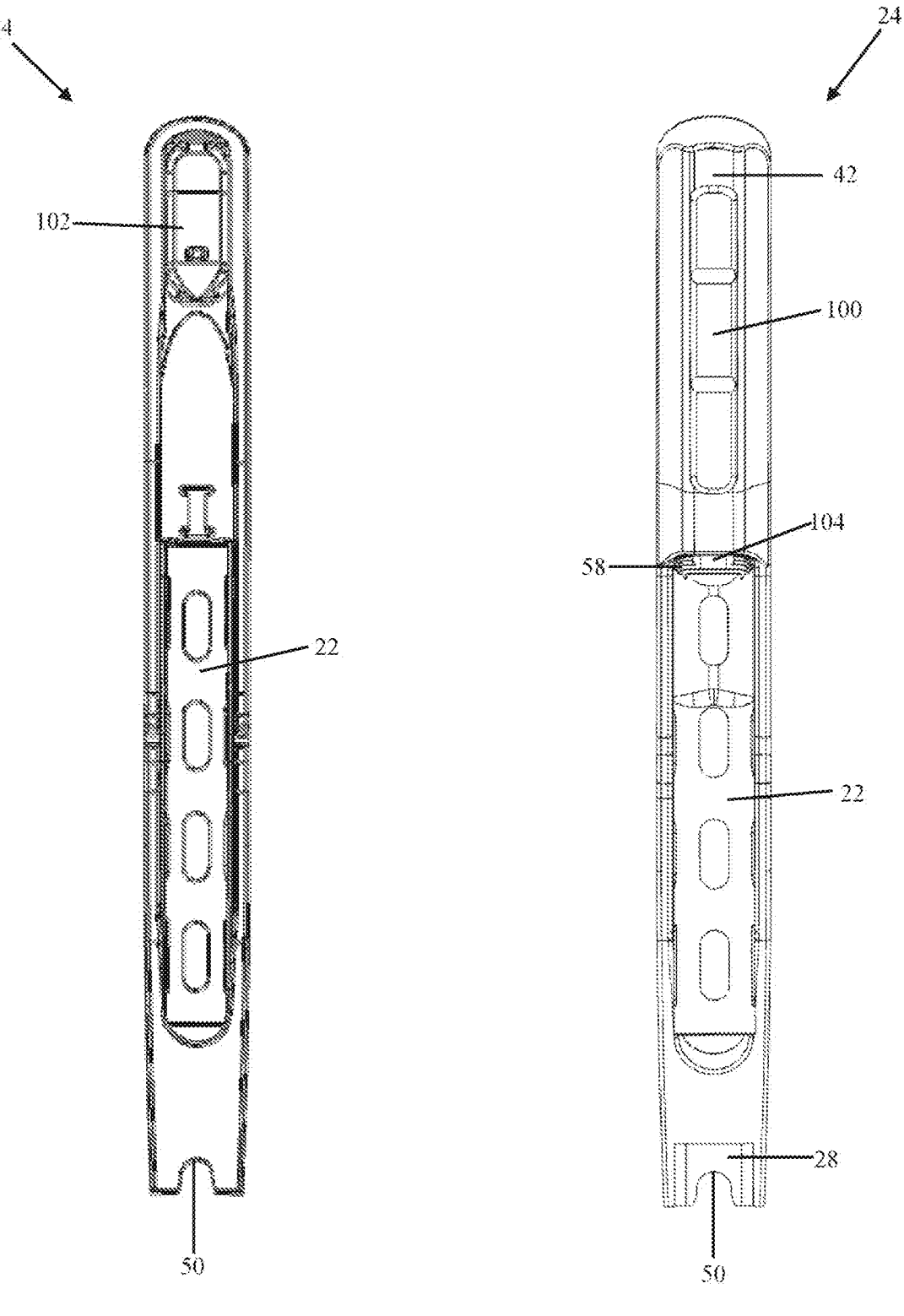
FIG. 5 is a front plan view of the compression lever and sleeve assembly of FIG. 2.
FIG. 6 is a rear plan view of the compression lever and sleeve assembly of FIG. 2.
Figure 7:
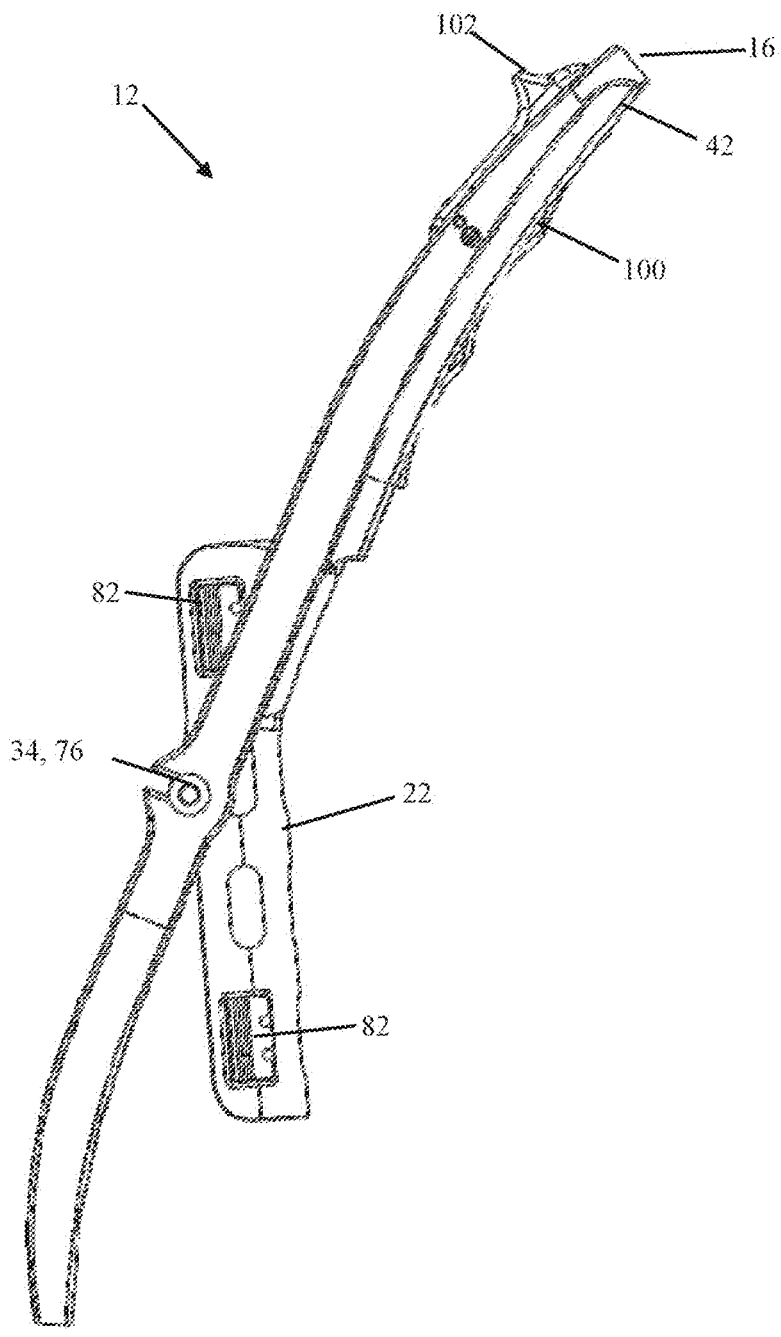
FIG. 7 is a side plan view of the compression lever and sleeve assembly of FIG. 2.

The compression lever 24 is positioned to allow relative pivot between itself and the stanchion member 16 without interference. Some embodiments of the compression lever 24 achieve this by means of a cutout 48 that is dimensioned to allow the sleeve 22 and the stanchion member 16 to pass through. As shown in FIGS. 2-4, positioning the sleeve 22 within a cutout 48 on the compression lever 24 allows the use of two pivot points 26 on either side of the sleeve 22 while still allowing a broad range of angular motion of the sleeve 22 relative to the compression lever 24.

The second bone anchor engagement feature 28, at the distal end 40 of the compression lever 24, is configured to reversibly attach the compression lever 24 to a bone anchor 118 so as to restrict movement between the lever 24 and the anchor 118. Various such configurations are known in the art. In addition, a notch 50 may be positioned at the distal end 40 of the compression lever 24 to accommodate the spinal rod 52. The dimensions of the 10 notch 50 will depend on the dimensions of the rod 52.

The overall geometry of the compression lever 24 may be designed to modulate the mechanical advantage of the lever system 32. As explained above, the position of the pivot point 26 (fulcrum) can be varied to modulate the mechanical advantage of the lever system 32. The shape of the compression lever 24 can also be curved to alter the position of the proximal (38) and/or distal (40) ends of the compression lever 24 relative to a straight lever. For example, in the embodiment of the compression lever 24 shown in FIGS. 13 and 14, the compression lever 24 contains two curves. The proximal end 38 is curved away from the stanchion member 16 in the proximal direction, which positions the hand grip 100 farther away from the stanchion member 16 than otherwise and increases the relative angle between the handgrip 100 and the stanchion member 16, allowing more comfortable use. The distal portion 40 of the compression lever 24 is also curved toward the stanchion member 16 In the distal direction, decreasing the distance between the first bone anchor engagement feature 20 at the bottom of the compression lever 24 and the second bone anchor engagement feature 28 at the bottom of the stanchion member 16. This permits the instrument 10 to be used with two bone anchors (118, 120) that are closer together than would be possible if the compression lever 24 was straight in the distal portion 40.

Figure 8:
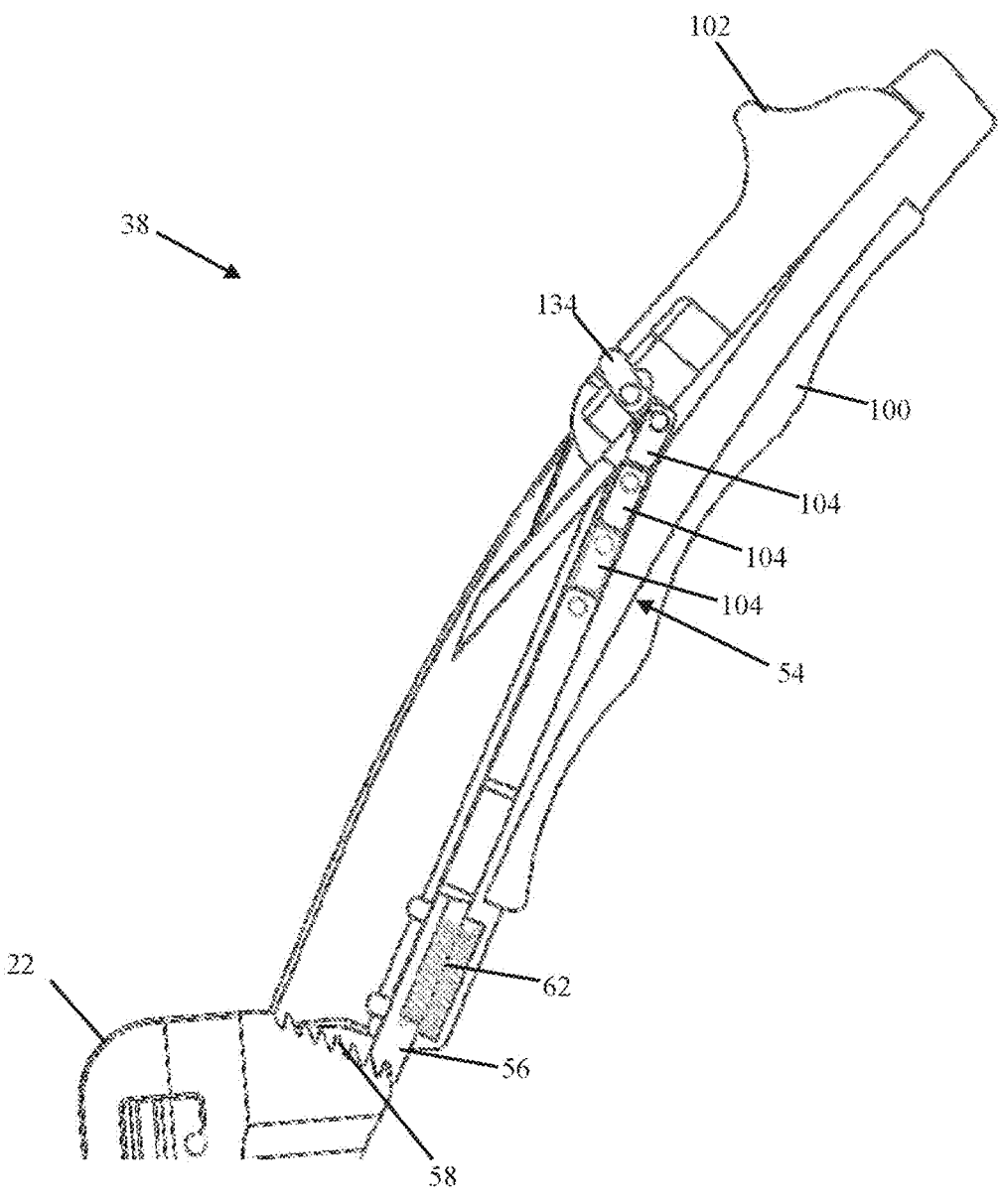
FIG. 8 is a cross-sectional view of the proximal portion of the compression lever and sleeve assembly of FIG. 2.

During operation, the user must lock the spinal rod in one of the bone anchors, exert compressing force between the compression lever 24 and the stanchion member 16 until the desired compression is achieved, lock the spinal rod 52 in the other bone anchor (118, 120), and then remove the compression instrument 10 from the surgical site. Compression must thus be maintained while the rod 52 is being locked into one or both of the bone anchors (1.18, 1.20), then released so that the instrument 10 can be removed. Maintaining this compression manually is difficult for a single user to do while simultaneously locking the rod 52 to the bone anchor 120 and often requires a second user (e.g., one to maintain manual compression using the compression instrument 10 and one to lock a locking element into place). To solve this problem, some embodiments of the instrument 10 and system 32 comprise an interface mechanism 54 that prevents the release of compression between the lever 24 and the stanchion member 16 until it is needed. An example of such an interface mechanism 54 is illustrated in FIG. 8. The interface mechanism 54 shown in FIG. 8 comprises a pawl 56 and ratchet system 32. Ratchet teeth 58 are present on the sleeve 22 that engage a pawl 56 on the compression lever 24. As the angle between the sleeve 22 and the compression lever 24 decreases (Le., they are compressed relative to one another), the pawl 56 slips to the next set of ratchet teeth 58, but due to the orientation of the ratchet teeth 58 the pawl 56 cannot move in the opposite direction. In the illustrated embodiment the pawl 56 is biased to extend into contact with the ratchet teeth 58 by a spring 62. The spring 62 is compressed between the pawl 56 and an elongate plunger 104. To release the force on the spring 62 exerted by the elongate plunger 104, a release mechanism 64 allows the plunger 104 to move away from the spring 62. In the illustrated embodiment this involves the use of a flexible plunger 104 in multiple segments held in place by a post 134; a release button 102 is pressed to reorient the post 134 to allow the plunger 104 to move freely. Without the plunger 104 pressing against the spring 62, the compression in the spring 62 ls released, and the spring 62 no longer pushes on the pawl 56 to impart bias, and so the pawl 56 retracts from engagement with the ratchet teeth 58.

The systems 32 and instruments 10 described above may be used in a method of compressing a first bone structure 12 containing a first bone anchor 118 relative to a second bone structure 14 containing a second bone anchor 120. In a general embodiment, the method comprises (in any order): assembling a stanchion member 16 having an elongate shaft 18 and a first bone anchor engagement feature 20 with a sleeve member 22 such that the sleeve member 22 at least partially encircles the stanchion member 16; pivotably connecting a compression lever 24 including a second bone anchor engagement feature 28 at a distal end 40 to the sleeve member 22 at a pivot point 26 to allow the compression lever 24 to rotate relative to the stanchion member 16 about an axis that contains the pivot point 26; engaging the first bone anchor engagement feature 20 to the first bone anchor: 1.18; engaging the second bone anchor engagement feature 28 to the second bone anchor 120; and compressing the first bone structure 12 relative to the second bone structure 14 by imparting force on a proximal end 38 of the compression lever 24 with a vector toward the stanchion member 16. In a specific embodiment of the method the steps are performed in the same order as listed. With reference to the method, the stanchion member 16, sleeve member 22, compression lever 24, and bone anchors (118, 120) may be any that are disclosed above as suitable for use in the instrument 10 or system 32.

Among other possible uses it is specifically contemplated that the method may be used to compress two vertebrae. Such intervertebral compression may involve the use of pedicle screws 124 as bone anchors 118 & 120 with a spinal rod 52 or other similar structure to fix the relative positions of the vertebrae in question. The method may further comprise introducing a locking element 78 (such as a locking cap or locking screw) into one or both of the pedicle screws 124. In a specific embodiment of the method a locking element 78 is introduced through the lumen 70 in the stanchion element, and then a driver tool is inserted through the lumen. 70 of the stanchion element to drive the locking element 78 into place over the spinal rod 52. Additional instruments 10 useful in spinal fusion techniques may be employed, as is known in the art.

It is to be understood that any given elements of the disclosed embodiments of the invention may be embodied in a single structure, a single step, a single substance, or the like.

Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skin and/or knowledge of a person having ordinary skill in the relevant art, The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

The invention claimed is:

1. A spinal compression system for compressing a first bone structure relative to a second bone structure, the system comprising:
   a stanchion having an elongate shaft and a first bone anchor engager at a distal end configured to engage a tulip portion of a first bone anchor;
   a sleeve comprising a first part of a pivot mechanism and configured to at least partially encircle the stanchion; and
   a compression lever comprising:
      a distal end configured to engage a tulip portion of a second bone anchor and comprising an opening configured to receive a spinal rod passing through tulip portions of the first and second bone anchors; and
      a second part of the pivot mechanism configured to reversibly connect to the first part of the pivot mechanism of the sleeve forming a pivot point to allow the compression lever to rotate relative to the stanchion about an axis that contains the pivot point.

2. The system of claim 1, wherein the distal end of the stanchion comprises a receptacle adapted to receive the tulip portion of the first bone anchor therein.

3. The system of claim 1, wherein the distal end of the compression lever comprises an indentation adapted to receive the tulip portion of the second bone anchor therein.

4. The system of claim 1, wherein the distal end of the stanchion comprises a rod recess dimensioned to admit the spinal rod at least partially therein and to permit the spinal rod to move unencumbered therethrough in a direction lengthwise with respect to the spinal rod.

5. The system of claim 1, wherein the compression lever comprises a hand grip at or adjacent a proximal end of the compression lever.

6. The system of claim 1, comprising an interface that controls a release of compression between the compression lever and the stanchion.

7. A spinal compression instrument for compressing a first bone structure relative to a second bone structure, the instrument comprising:
   a stanchion having:
      an elongate shaft with a distal end and a proximal end;
      a first bone engager at the distal end of the elongate shaft;
      a rod recess in the first bone engager dimensioned to accept a spinal rod;
   a sleeve at least partially encircling the stanchion, the sleeve having:
      a pair of generally planar sidewalls;
      a stanchion channel between the pair of sidewalls;
      a pair of pivot posts protruding outwardly;
      a plurality of ratchet teeth at a proximal end of the sleeve; and
      a snap-fit mechanism positioned to temporarily secure the stanchion within the stanchion channel;
   a compression lever comprising a cutout extending between a proximal end and a distal end of the compression lever, wherein the stanchion and sleeve extend through the cutout, and the compression lever is pivotably connected to the sleeve via a pair of pivot connectors engaged to the pair of pivot posts at a pivot point located between a proximal end and a distal end of the cutout to allow the compression lever to rotate relative to the stanchion about an axis that contains the pivot posts.

8. The spinal compression instrument of claim 7, wherein the compression lever further comprises:
   a second bone anchor engager at a distal end;
   a notch in the distal end dimensioned to admit a spinal rod; and
   a back surface that faces away from the stanchion that includes a handle grip.

9. The spinal compression instrument of claim 7, wherein the compression lever further comprises:
   a retractable pawl capable of assuming an extended position in which the pawl is engaged to the ratchet teeth and a retracted position in which the pawl is disengaged from the ratchet teeth, wherein the pawl is biased toward the extended position; and
   a bias release switch configured to de-bias the retractable pawl.

10. The instrument of claim 7, wherein the distal end of the stanchion comprises a receptacle adapted to receive a tulip portion of a first bone anchor therein.

11. The instrument of claim 7, wherein a distal end of the compression lever comprises an indentation adapted to receive a tulip portion of a second bone anchor therein.

12. The instrument of claim 7, wherein the distal end of the stanchion comprises a rod recess dimensioned to admit the spinal rod at least partially therein and to permit the spinal rod to move unencumbered therethrough in a direction lengthwise with respect to the spinal rod.

13. The instrument of claim 7, comprising an interface that controls a release of compression between the compression lever and the stanchion.

\* \* \* \* \*